United States Patent
Mack et al.

(10) Patent No.: US 7,098,371 B2
(45) Date of Patent: Aug. 29, 2006

(54) METHOD OF HYDRODECHLORINATING NUCLEAR-CHLORINATED ORTHO-XYLENES

(75) Inventors: Karl-Ernst Mack, Wiesbaden (DE); Daniel Decker, Liederbach a. Ts. (DE)

(73) Assignee: Clarient GmbH, Frankfurt (DE)

( * ) Notice: Subject to any disclaimer, the term of this patent is extended or adjusted under 35 U.S.C. 154(b) by 289 days.

(21) Appl. No.: 10/659,600

(22) Filed: Sep. 10, 2003

(65) Prior Publication Data

US 2004/0054245 A1 Mar. 18, 2004

(30) Foreign Application Priority Data

Sep. 12, 2002 (DE) ............................... 102 42 223

(51) Int. Cl.
*C07C 1/26* (2006.01)
(52) U.S. Cl. .................................................. 585/469
(58) Field of Classification Search ................ 585/469
See application file for complete search history.

(56) References Cited

U.S. PATENT DOCUMENTS

| | | | | |
|---|---|---|---|---|
| 3,493,626 | A | 2/1970 | Zorn et al. .................. | 260/668 |
| 4,190,609 | A | 2/1980 | Lin .......................... | 260/650 R |
| 4,289,916 | A | 9/1981 | Nakayama et al. ......... | 570/209 |
| 4,444,983 | A | 4/1984 | Hattori et al. .............. | 570/209 |
| 4,647,709 | A | 3/1987 | Wolfram .................... | 570/209 |
| 5,177,268 | A | 1/1993 | Balko et al. ................ | 568/726 |
| 5,552,549 | A | 9/1996 | Rasp et al. ................. | 546/139 |
| 5,625,110 | A | 4/1997 | Schoedel et al. ........... | 585/641 |
| 2002/0049357 | A1 | 4/2002 | Mais ......................... | 570/237 |

FOREIGN PATENT DOCUMENTS

| | | |
|---|---|---|
| EP | 0 126 669 | 11/1984 |
| EP | 0 173 222 | 3/1986 |
| WO | WO 02/14245 | 2/2002 |

OTHER PUBLICATIONS

Miroslav Uhlir, et al. "Catalytic Hydrogenolysis of hexachlorobenzene to lower-chlorinated benzenes", Chemical Abstracts, 114:121703n, 1991.
English abstract for EP 0126669, Nov. 28, 1984.
Helmut Zahn et al., "DL-hydroxylysim und DL-allohydroxylysin und ihre lactone", Chemische Berichte Jahrg. 91, 1958, pp. 1359-1379.
Ullman's Encylopadia of Industrial Chemistry, 5th edition, vol. A8, pp. 211-215.
"Selective para chlorination of o-Xylene over zeolite catalysts", Journal of Catalysis, 150, 1994, pp. 430-433.
Sudip Mukhopadhyay et al., "Palladium-catalyzed Aryl-Aryl coupling in water using molecular hydrogen: kinetics and process optimization of a solid-liquid-gas system", Tetrahedron, 55, 1999, pp. 14763-14768.
Chemical abstract, CA 1998, Nr. 472737.
Chemical abstract, CA 1991, Nr. 514135.

*Primary Examiner*—Thuan D Dang
(74) *Attorney, Agent, or Firm*—Richard P. Silverman

(57) ABSTRACT

Method of hydrodechlorinating nuclear-chlorinated o-xylenes and recovering o-xylene, forming hydrogen chloride, the nuclear-chlorinated o-xylenes being hydrogenated in the gas phase at a noble-metal-containing catalyst at a temperature in the range from 220 to 360° C. The catalyst preferably comprises palladium or platinum, in particular supported palladium or platinum. The nuclear-chlorinated o-xylenes can be used individually or as mixtures.

15 Claims, No Drawings

METHOD OF HYDRODECHLORINATING NUCLEAR-CHLORINATED ORTHO-XYLENES

Nuclear-chlorinated ortho-xylenes, in particular nuclear-monochlorinated o-xylenes, are important starting materials for preparing agricultural and pharmaceutical products.

In the preparation of nuclear-monochlorinated o-xylenes by chlorinating o-xylene, with increasing conversion rate of o-xylene, nuclear-dichlorinated o-xylenes are also unavoidably formed and, to a small extent also, nuclear-trichlorinated o-xylenes. The nuclear-polychlorinated o-xylenes, because of their low value, must frequently be disposed of as wastes. This requires, in the case of incineration, for example, a particularly high expenditure because of the hazard of dioxin formation.

Furthermore, of the nuclear-monochlorinated o-xylenes, frequently only one of the two isomers formed is used further industrially, so that that isomer having a lower value must also be considered as waste and disposed of. Frequently, 4-chloro-1,2-dimethylbenzene is the more sought-after isomer. 3-Chloro-1,2-dimethylbenzene is therefore removed from the desired isomer by distillation, for example, frequently disposed of by incineration, as with the nuclear-polychlorinated o-xylenes, and thus increases the unwanted surplus consumption of the o-xylene starting material.

Since in the usual case of chlorinating o-xylene in the presence of Lewis acids, the two isomers 4-chloro- and 3-chloro-1,2-dimethylbenzene are produced in a ratio of less than 1.5:1 (equivalent to less than 60%:40%) considerable efforts have been undertaken by adding co-catalysts to obtain a shift in the isomer ratio in the direction of the respective desired isomer.

Co-catalysts which have been mentioned as effective for enhancing the formation of 4-chloro-1,2-dimethylbenzene are, for example, the thianthrenes class of compound (U.S. Pat. No. 4,190,609), which are, however, considered to be highly toxic, or the thiazepines or thiazocines class (WO 02/14245), which are compounds which are very difficult to synthesize, however, because of a highly demanding pattern of substituents. However, even in the most favorable cases of shifting the isomer ratios, the unwanted isomers are produced in an amount of at least 25% by weight, based on the weight of the desired isomer.

Furthermore, because in the chlorination of o-xylene, with increasing conversion rate, the unwanted nuclear-polychlorinated products are also unavoidably produced, the conversion rate of o-xylene is frequently restricted. This means that unreacted o-xylene must be recovered from the reaction mixture with relatively high expenditure on distillation.

It was therefore an object of the invention to provide, for economic and ecological reasons, a method which permits 4-chloro-1,2-dimethylbenzene and/or 3-chloro-1,2-dimethylbenzene to be prepared substantially without inevitable production of the respective unwanted isomer and the nuclear-polychlorinated o-xylenes.

This object has been achieved in a surprisingly simple manner by the respective unavoidably produced products being isolated and converted to o-xylene and hydrogen chloride by treatment at elevated temperature with hydrogen at a noble-metal-containing catalyst, as a result of which o-xylene can be fed back to the chlorination reaction and the resultant hydrogen chloride can be worked up to give industrially valuable hydrochloric acid.

The invention thus relates to a method of hydrodechlorinating nuclear-chlorinated o-xylenes in the gas phase at a noble-metal-containing catalyst with recovery of o-xylene and with the formation of hydrogen chloride at a temperature in the range from 220 to 360° C. The nuclear-chlorinated o-xylenes produced as byproduct can be used individually or as mixtures.

The hydrodechlorination of polychlorinated benzene derivatives is known. Reactions in the liquid phase, for example using Raney nickel and hydrogen (Chem. Ber. 91 (1958), 1376) or, for example, using palladium on carbon (U.S. Pat. No. 5,177,268) generally proceed at temperatures around 100° C. at a hydrogen overpressure, frequently using a solvent, and disadvantageously with addition of bases for neutralizing the resultant hydrogen chloride. The chlorides produced have to be separated off and disposed of, and the solvent if appropriate recovered. This also applies to the example of hydrodechlorinating 4-chloro-1,2-dimethylbenzene using palladium on carbon in aqueous sodium hydroxide solution at 110° C. and 4 bar hydrogen pressure, in which, however, considerable amounts of unwanted byproducts are formed. o-Xylene recovery in this case is only less than 40% (Tetrahedron 55; 51; 1999; 14763).

The addition of base can frequently be avoided by working in the gas phase. However, in this case there is the problem that, for thermodynamic reasons, in the temperature range below 300° C., nuclear hydrogenation takes place preferentially with the formation of the corresponding cyclohexane derivatives (Ullmann's Encyclopedia of Industrial Chemistry, 5$^{th}$ Edition, Volume A8, p. 211 (1987)). Typically, trichlorobenzene, for example, is completely dechlorinated and hydrogenated to cyclohexane in the presence of a supported palladium catalyst at temperatures up to 200° C. (U.S. Pat. No. 5,625,110).

The disadvantageous hydrogenation of the benzene nucleus can be decreased, as is known, by employing higher temperatures, for example as in U.S. Pat. No. 5,552,549 in the case of hydrodechlorinating polychlorobenzenes at temperatures around 400° C. However, in this case, complete dechlorination to benzene is not achieved.

Surprisingly, it has now been found that the hydrodechlorination of nuclear-chlorinated o-xylenes can be carried out in the gas phase in the temperature range from 220 to 360° C. in the presence of noble-metal catalysts in high yield of around 90%, and with long service lives of the catalysts. This was particularly surprising since precisely the temperature range around 300° C. is successfully employed, in which, owing to the relatively low temperature, firstly a considerable extent of 1,2-dimethylcyclohexane formation would be expected, and secondly complete dechlorination, particularly of nuclear-polychlorinated o-xylenes, was still not expected.

The catalyst preferably comprises as noble metals palladium and/or platinum or compounds of these metals; preferably it comprises palladium, supported on an oxidic material such as aluminum oxide or silicon oxide or carbon. Particular preference is given to the use of palladium-containing catalysts on carbon.

The content of noble metal on the support material can be varied within broad ranges from 0.01 to 5% by weight. Preference is given to a content of from 0.1 to 3% by weight, particular preference to from 0.5 to 1.5% by weight.

The hourly charge of the catalyst with starting material can be in the range from 0.05 to 4 liters of liquid per liter of catalyst. An hourly charge from 0.1 to 1 liter of liquid is expedient, a charge of from 0.2 to 0.5 liters per liter of catalyst is particularly expedient.

The molar ratio of nuclear monochlorinated to nuclear polychlorinated o-xylenes can have any desired value in the starting material. Preference is given to the mixture produced in the method of chlorinating o-xylene under economic aspects which has ratios from 5:1 to 1:2.

The amount of hydrogen fed is to be at least the equimolar equivalent of the molar content of chlorine in the starting material. The use of a hydrogen excess is expedient which can be from 3 to 30 times the molar amount, in particular from 5 to 20 times the molar amount, and is to be determined for the individual case as a function of the activity of the catalyst and if appropriate the degree of dilution of the starting mixture of nuclear-chlorinated o-xylenes and hydrogen with an inert gas, for example nitrogen.

The hydrodechlorination can be carried out under atmospheric pressure or elevated pressure. For technical and equipment reasons, however, the atmospheric pressure procedure is to be preferred.

The temperature prevailing in the catalyst bed can be varied in the range from 220° C. to 360° C. However, it is to be at least high enough that no condensation of the nuclear-chlorinated o-xylenes takes place in the reactor. Preference is given to the temperature range from 260 to 350° C., particular preference from 280 to 330° C.

The inventive method is carried out, for example in such a manner that o-xylene is chlorinated in one of the manners described in the outset. The reaction mixture is then fractionated by distillation into the desired product and the unwanted nuclear-monochlorinated o-xylene. The nuclear-dichlorinated o-xylenes are isolated from the bottom phase of this distillation and are either passed separately or in a mixture with the nuclear-monochlorinated o-xylene produced as unwanted byproduct over the catalyst in the above-described manner as vapor phase starting material together with hydrogen. o-Xylene is produced from the reaction mixture by condensation at a high purity of >95%, in particular from 97 to 99%, and, depending on the quality of the condensation, in yields of greater than 85%, in particular from 90 to 95%. The hydrogen chloride present in the exhaust gas is absorbed in water to give hydrochloric acid. The service life of the catalyst, when the above-described preferred loading limits with starting material are met, is at least 700 hours before it, by means of one or more regenerations using small amounts of air at reaction temperature, is consistently virtually completely retained at its original activity.

On account of the reuse of the recovered o-xylene, it is possible to achieve virtually quantitative yields of the respectively wanted nuclear-monochlorinated o-xylene, with the production of very small amounts of waste. In addition, the inventive method also permits o-xylene to be consistently completely reacted in the chlorination each time according to economic aspects and thus advantageously to be able to avoid its recovery by distillation from the reaction mixture.

The examples below are to illustrate the inventive method without restricting it thereto.

EXAMPLE 1

50 ml (approximately 25 g) of a catalyst containing 1% by weight of palladium are applied to granulated carbon in a vertical glass tube (diameter 3.5 cm) in an electrically heated oven. The temperature in the catalyst bed is brought to 290° C., while a mixture of in each case 40 l/h of hydrogen and nitrogen is passed through. After a further hour under these conditions, in addition, 15 g/h of a mixture of virtually equal proportions of 4-chloro-1,2-dimethylbenzene and 3-chloro-1,2-dimethylbenzene are added continuously. Evaporation takes place on a layer of glass bodies above the catalyst. As a result of the reaction which begins immediately, a temperature of 310° C. in the catalyst is established. The reactor discharge is cooled to approximately 25° C., a colorless liquid condensing. Gas-chromatographic analysis found o-xylene in a purity of greater than 98%. Over a period of 680 hours, a mean 10 g of condensate are produced, equivalent to a yield around 90% of o-xylene.

A slightly decreasing catalyst activity after about 500 hours of operating time can be compensated for by increasing the hydrogen proportion in the gas stream to 50 l/h.

This example shows that not only the 4-chloro-isomer, but also the 3-chloro-isomer is dechlorinated in an identical quality.

EXAMPLE 2

Example 1 is repeated, in which case, however, then 15 g/h of a mixture of 20% by weight of 4-chloro-1,2-dimethylbenzene and 80% by weight of an isomer mixture of nuclear-dichlorinated o-xylenes is added. The temperature establishes itself at 320° C. In the course of 240 h at a constant catalyst activity, per hour a mean 10 g of o-xylene is obtained in high purity (>98.5%) equivalent to a yield of approximately 92%.

This example shows that nuclear-monochlorinated and nuclear-dichlorinated o-xylenes are dechlorinated in the same quality.

EXAMPLE 3

This example illustrates the advantage of the inventive hydrodechlorination in association with the chlorination of o-xylene.

6784 g (64 mol) of o-xylene are placed in a jacketed vessel having an inner diameter of 15 cm and a height of 90 cm, 3.4 g of the co-catalyst described in EP-A-0 173 222, tetrachlorinated 2,8-dimethylphenoxathiine, are dissolved therein and at 20° C. 4544 g (64 mol) of chlorine are introduced via a glass frit at the bottom of the reactor in the course of 5 hours. A bed of iron rings is situated around the glass frit. The temperature in the reactor is kept at 20° C. by cooling. Gas-chromatographic analysis of the 8900 g of reaction discharge found 6.9% of o-xylene, 65.6% of 4-chloro-1,2-dimethylbenzene, 21.4% of 3-chloro-1,2-dimethylbenzene, 5.5% of dichlorinated o-xylene and 0.3% of high-boilers. This gave a yield of 4-chloro-1,2-dimethylbenzene, based on reacted o-xylene, of 71.5%. Work-up by distillation produced, as distillates, 1900 g of 3-chloro-1,2-dimethylbenzene, and 490 g of dichlorinated o-xylene, in addition to 30 g of high-boilers as bottom phase.

The mixture of the distillates (2390 g) is hydrodechlorinated similarly to Example 1 for an addition time of 160 hours. 1560 g of o-xylene are produced at a purity of 98.5%, and, if required, can be fed back to the chlorination reaction after purification by distillation.

On account of the recovery of o-xylene, the yield of 4-chloro-1,2-dimethylbenzene improves from 71.5 to greater than 95%.

The invention claimed is:

1. A method of hydrodechlorinating nuclear-chlorinated o-xylenes which consists of hydrodechlorinating in a single reactor a starting material comprising a nuclear-chlorinated o-xylene or mixtures of nuclear-chlorinated o-xylenes in the gas phase with a gas stream comprising hydrogen in the presence of a noble-metal-containing catalyst at a temperature in the range from 220 to 360° C. to provide a reactor effluent comprising at least 90%-wt yield of o-xylene and hydrogen chloride, and recovering the o-xylene.

2. The method as claimed in claim 1, wherein the noble-metal-containing catalyst comprises a noble metal selected from the group consisting of palladium, platinum, and mixtures thereof.

3. The method as claimed in claim 1, wherein the noble-metal-containing catalyst comprises a noble metal disposed on a support material comprising an oxidic material.

4. The method as claimed in claim 1, wherein the hydrogen is fed to said single reactor in at least an equimolar equivalent of the molar content of nuclear-chlorinated o-xylene in the starting material.

5. The method as claimed in claim 1, wherein the nuclear-chlorinated o-xylene is selected from the group consisting of nuclear monochlorinated o-xylene, nuclear polychlorinated o-xylene and mixtures thereof.

6. The method as claimed in claim 1, wherein the hydrodechlorinating reaction is carried out at atmospheric pressure.

7. The method as claimed in claim 2, wherein the noble-metal-containing catalyst comprises from 0.01 to 5 percent by weight of said noble metal and a support material.

8. The method as claimed in claim 3, wherein the noble-metal-containing catalyst comprises a noble metal disposed on a support material selected from the group consisting of aluminum oxide; silicon oxide; carbon, and mixtures thereof.

9. The method as claimed in claim 1, wherein a molar ratio of the hydrogen to an equivalent molar content of nuclear-chlorinated o-xylene in the starting material ranges from 3 to 30 times said equivalent molar content.

10. The method as claimed in claim 1, wherein the starting material comprises a mixture of nuclear monochlorinated o-xylene and nuclear polychlorinated o-xylene in a molar ratio of from 5:1 to 1:2.

11. The method of claim 1, wherein the support material is carbon.

12. A method for the dehydrochlorination of mixed nuclear-chlorinated o-xylenes, said method consisting of:
    a) passing a gas stream comprising hydrogen and a starting material comprising the mixed nuclear chlorinated o-xylenes, to a single reactor and therein contacting a noble metal catalyst at a temperature in the range from 220 to 360° C. to dehydrochlorinate the mixed nuclear chlorinated o-xylenes and to provide a reactor discharge comprising at least 90%-wt yield of o-xylene and hydrogen chloride, and
    b) recovering the o-xylene from the reactor effluent, wherein said mixed nuclear chlorinated o-xylenes are selected from the group consisting of nuclear monochlorinated o-xylenes, nuclear polychlorinated o-xylenes and mixtures thereof and wherein the noble metal catalyst comprises a noble metal selected from the group consisting of palladium, platinum, and mixtures thereof.

13. The method of claim 12, wherein said noble metal catalyst comprises the noble metal disposed on a support material selected from the group consisting of aluminum oxide, silicon oxide, carbon and mixtures thereof.

14. The method of claim 12, wherein step b) comprises fractionation wherein an o-xylene product is recovered and an unwanted byproduct stream comprising nuclear monochlorinated and nuclear dichlorinated o-xylene is combined with the starting material and returned to the single stage reaction zone.

15. The method of claim 12, wherein said noble metal catalyst is periodically regenerated with air at said reaction temperature.

\* \* \* \* \*